United States Patent [19]

Kurazumi et al.

[11] Patent Number: 5,348,744
[45] Date of Patent: * Sep. 20, 1994

[54] ANTIDIARRHEAL COMPOSITIONS CONTAINING LOPERAMIDE HYDROCHLORIDE AND A SACCHARIDE

[75] Inventors: Toshiaki Kurazumi, Narita; Hiroyuki Mizuno, Chiba; Katsumi Imamori; Akira Iwasa, both of Yotsukaido, all of Japan

[73] Assignee: SS Pharmaceutical Co., Ltd., Tokyo, Japan

[*] Notice: The portion of the term of this patent subsequent to Jan. 26, 2010 has been disclaimed.

[21] Appl. No.: 944,232

[22] Filed: Sep. 14, 1992

Related U.S. Application Data

[63] Continuation of Ser. No. 780,931, Oct. 23, 1991, Pat. No. 5,182,112.

[30] Foreign Application Priority Data

Oct. 24, 1990 [JP] Japan ................................ 2-286458

[51] Int. Cl.$^5$ ...................... A61K 31/445; A61K 9/14
[52] U.S. Cl. .................................. 424/439; 424/461; 424/488; 424/499; 514/867
[58] Field of Search .................. 424/439, 440, 441; 514/317, 867, 23, 53

[56] References Cited

U.S. PATENT DOCUMENTS

| | | | |
|---|---|---|---|
| 4,666,716 | 5/1987 | Sheth et al. | 434/195.1 |
| 4,764,604 | 8/1988 | Muller | 536/103 |
| 4,824,853 | 4/1989 | Wals et al. | 514/327 |
| 4,873,229 | 10/1989 | Deya et al. | 514/54 |
| 5,028,437 | 7/1991 | Jerrett | 424/535 |
| 5,182,112 | 1/1993 | Kurazumi et al. | 424/439 |
| 5,219,573 | 6/1993 | Tarka, Jr. et al. | 424/439 |

FOREIGN PATENT DOCUMENTS

| | | |
|---|---|---|
| 2014377 | 10/1990 | Canada . |
| 0393909 | 10/1990 | European Pat. Off. . |
| 0428296 | 5/1991 | European Pat. Off. . |

OTHER PUBLICATIONS

Chemical Abstracts, vol. 113, No. 22, 1991, & JP-A-0-2-096526, Apr. 9, 1990, S. Yamazaki, et al., "Manufacture Of Pharmaceutical Powders Containing Loperamide".

*Primary Examiner*—Thurman K. Page
*Assistant Examiner*—Neil Levy
*Attorney, Agent, or Firm*—Oblon, Spivak, McClelland, Maier & Neustadt

[57] ABSTRACT

Described herein are antidiarrheal compositions containing loperamide hydrochloride as an effective ingredient and a saccharide, for example, a monosaccharide, oligosaccharide or sugar alcohol in an amount as much as at least 3,000 times the weight of loperamide hydrochloride.

6 Claims, No Drawings

ANTIDIARRHEAL COMPOSITIONS CONTAINING LOPERAMIDE HYDROCHLORIDE AND A SACCHARIDE

The present application is a continuation of application Ser. No. 07/780,931, filed on Oct. 23, 1991, now U.S. Pat. No. 5,182,112.

BACKGROUND OF THE INVENTION

1) Field of the Invention

This invention relates to antidiarrheal compositions with loperamide hydrochloride contained therein, and more specifically to antidiarrheal compositions which enhance the antidiarrheal efficacy of loperamide hydrochloride yet contain less loperamide hydrochloride to reduce development of its side effects.

2) Description of the Related Art

Of gastrointestinal symptoms, the most frequent is diarrhea. Diarrhea is known to be induced by an increase of peristalsis due to inflammation of the enteromucosa by a cause such as infection by a virus or bacterium, emotion or psychogenesis, overeating or the eating of spoiled food or the like.

If taken into consideration that diarrhea is a biodefense reaction for earlier excretion of a substance toxic to the living body, early recourse to the use of an antidiarrheal should be avoided.

Diarrhea may however result in serious dehydration unless proper treatment is applied. Administration of an antidiarrheal agent as early as possible is desired as a symptomatic therapy in such a case.

As symptomatic therapeutic agents for diarrhea, chemotherapeutic agents, astringents, atropine preparations and the like have been used to date depending on their causes. Further, opium and morphine are also known to induce spasticity of the intestinal smooth muscle and peristaltic ataxia to provide antidiarrheal effect.

However, morphine has the potential danger of addiction such as dependence due to central effects. It has therefore been considered necessary for many years to separate central effects and intestinal effects from each other in the use of morphine as an antidiarrheal agent.

Loperamide hydrochloride, which has been developed recently as an antidiarrheal agent, selectively acts on the intestinal tract to suppress peristalsis, and to reduce the secretion of water and electrolytes from the intestinal tract and promotes their absorption. At the same time, loperamide hydrochloride exhibits strong antidiarrheal efficacy and shows low central effects. Loperamide hydrochloride is therefore said to be an antidiarrheal agent having a broad safety zone. Capsules and powders containing it are already on the market.

Although loperamide hydrochloride has relatively few side effects it is not completely free of them. It may lead to oversensitivity such as efflorescence, urticaria or itching; symptoms such as drowsiness, hypotonicity and mydriasis in the central neural system; and symptoms such as abdominal distension, abdominal discomfort, nausea, vomiting, anorexia, unpleasant oral feeling and abdominal pain in the digestive system. It is therefore preferable to reduce the dosage, especially for infants.

It has therefore been desirable to develop a loperamide-hydrochloride-containing antidiarrhea composition which, even when the dosage of loperamide hydrochloride is small, still provides positive diarrhea control but gives reduced side effects.

SUMMARY OF THE INVENTION

With the foregoing in view, the present inventors have carried out an intensive investigation. As a result, it has been found that the addition of a saccharide in a predetermined amount to loperamide hydrochloride can improve the antidiarrheal effects of loperamide hydrochloride to a significant extent and can thus permit a reduced dosage, leading to the completion of the present invention.

In one aspect of the present invention, there is thus provided an antidiarrheal composition which comprises loperamide hydrochloride as an effective ingredient and a saccharide in an amount as much as at least 3,000 times the weight of loperamide hydrochloride.

The antidiarrheal efficacy of loperamide hydrochloride is enhanced owing to the addition of the saccharide in the antidiarrheal composition according to the present invention. This allows to reduce the dosage of loperamide hydrochloride, thereby making it possible to reduce its side effects.

DETAILED DESCRIPTION OF THE INVENTION AND PREFERRED EMBODIMENTS

Examples of saccharides usable in the present invention include monosaccharides, oligosaccharides and sugar alcohols. Described specifically, sucrose, fructose, glucose, sorbitol, xylitol, mannitol and the like can be mentioned as preferred examples. These saccharides can be used either singly or in combination. It is necessary to add such a saccharide in an amount as much as at least 3,000 times the weight of loperamide hydrochloride. The antidiarrheal efficacy is enhanced as the amount of the saccharide increases.

It is however impossible to add the saccharide in any extremely large amount when the dosage of loperamide hydrochloride per administration is taken into consideration. The upper limit is therefore about 50,000 times by weight or so, and amounts greater than this upper limit are impractical.

If the amount of the saccharide is smaller than 3,000 times by weight, on the other hand, no substantial improvement can be recognized in the antidiarrheal efficacy of loperamide hydrochloride, thereby failing to achieve the object of the present invention.

No particular limitation is imposed on the preparation form of the composition according to the present invention, a syrup or a dry syrup is preferred.

Upon preparation of a syrup, the pH may be adjusted to an acidic side to form loperamide hydrochloride as a solution system or to a neutral or basic side to provide a suspension system. Examples of pH regulators usable for this purpose include hydrochloric acid, sodium hydroxide, citric acid and sodium citrate. Upon preparation of a suspension, addition of a crystalline cellulose and sodium carboxymethylcellulose mixture, sodium carboxymethylcellulose, hydroxypropylcellulose, hydroxypropylmethylcellulose or the like is preferred so that a homogeneous suspension can be provided.

The syrup may additionally contain an antiseptic such as sodium benzoate or a paraoxybenzoate ester; and, as a stabilizer, a surfactant usable in oral preparations, such as polysorbate 80, polyoxyethylene hydrogenated castor oil, polyoxyethylene polyoxypropylene glycol or a sugar ester.

To form a dry syrup or other preparations, it is only necessary to add known excipients, lubricants, binders, corrigents, colorants and the like in combination as needed.

Since the antidiarrheal efficacy of loperamide hydrochloride has been enhanced owing to the addition of the saccharide in the antidiarrheal composition according to the present invention, it is possible to reduce the dosage in terms of loperamide hydrochloride. In general, loperamide hydrochloride is administered by dividing its daily dosage of 1-2 mg in 1-2 portions. Depending on the amount of the saccharide, for example, when the saccharide is added in an amount as much as at least 3,000 times the weight of loperamide hydrochloride, the use of the antidiarrheal composition of this invention can provide antidiarrheal efficacy even at a loperamide hydrochloride dosage about one third the conventional dosage thereof.

The present invention will hereinafter be described in further detail by tests and examples. It is however to be borne in mind that the present invention is not limited whatsoever by the following tests and examples.

TEST 1

Inhibitory action of loperamide hydrochloride itself for diarrhea induced by castor oil in rats was investigated firstly.

Employed as test drugs were 0.01, 0.003, 0.001 and 0.0003 wt.% aqueous solutions of loperamide hydrochloride, which had been adjusted to pH 4 with a citrate buffer. Wistar female rats (10 rats a group) which had been fasted for 24 hours were provided as experimental animals for the experiment. Each test drug was orally administered at the rate of 10 ml/kg to the rats and, 1 hour later, 1 ml of castor oil was administered further through the oral route.

The antidiarrheal action was judged depending on whether the diarrhea still continued or not at the 1st, 2nd, 3rd, 4th and 5th hours after the administration of castor oil. The results are shown in Table 1.

TABLE 1

Inhibitory Action of Loperamide Hydrochloride Itself for Diarrhea Induced by Castor Oil in Rats

| Dosage of test compound | N* | Number of rats whose diarrhea was inhibited at respective hours after administration of castor oil | | | | |
|---|---|---|---|---|---|---|
| | | 1st | 2nd | 3rd | 4th | 5th (hr) |
| Control | 10 | 0 | 0 | 0 | 0 | 0 |
| 1.0 mg/kg | 10 | 8 | 4 | 3 | 2 | 0 |
| 0.3 | 10 | 0 | 0 | 0 | 0 | 0 |
| 0.1 | 10 | 0 | 0 | 0 | 0 | 0 |
| 0.03 | 10 | 0 | 0 | 0 | 0 | 0 |

*N: Number of rats

According to the above results, no antidiarrheal efficacy was observed at loperamide hydrochloride dosages not greater than 0.3 mg/kg. Evaluation was therefore conducted at the dosage of 0.3 mg/kg in the following experiments.

TEST 2

Seven types of compositions were prepared by adding 0, 4.5, 6, 9, 15, 30 and 45 wt.% of sucrose to 0.003 wt.% of loperamide hydrochloride, respectively, followed by the adjustment to pH 4 with citrate buffer. A test was then conducted in a similar matter to Test 1. The results are summarized in Table 2. All designations of "times" will hereinafter mean "times by weight".

TABLE 2

Inhibitory Action of Syrup for Diarrhea Induced by Castor Oil in Rats

| Dosage of test syrup | Sucrose | Sucrose/loperamide | N* | Number of rats whose diarrhea was inhibited at respective hours after administration of castor oil | | | | |
|---|---|---|---|---|---|---|---|---|
| | | | | 1st | 2nd | 3rd | 4th | 5th (hr) |
| Control | | | 10 | 0 | 0 | 0 | 0 | 0 |
| 0.3 mg/kg | 0% | | 10 | 0 | 0 | 0 | 0 | 0 |
| 0.3 mg/kg | 4.5 | 1,500 times | 10 | 0 | 0 | 0 | 0 | 0 |
| 0.3 mg/kg | 6 | 2,000 | 10 | 0 | 0 | 0 | 0 | 0 |
| 0.3 mg/kg | 9 | 3,000 | 10 | 2 | 1 | 0 | 0 | 0 |
| 0.3 mg/kg | 15 | 5,000 | 10 | 3 | 1 | 0 | 0 | 0 |
| 0.3 mg/kg | 30 | 10,000 | 10 | 5 | 3 | 1 | 0 | 0 |
| 0.3 mg/kg | 45 | 15,000 | 10 | 10 | 6 | 2 | 0 | 0 |

*N: Number of rats

It is envisaged from the above results that, even at the loperamide hydrochloride dosage of 0.3 mg/kg where no antidiarrheal action is observed as long as loperamide hydrochloride is used singly, antidiarrheal efficacy can be expected from the combined use of a saccharide as much as 3,000 times or more loperamide hydrochloride and, above this level, a higher saccharide concentration results in higher antidiarrheal efficacy.

EXAMPLE 1

A syrup of the following formulation was prepared by the below-described preparation procedure.

| <Formulation> | |
|---|---|
| Loperamide hydrochloride | 3 mg |
| Sucrose | 45 g |
| Citric acid | 100 mg |
| Sodium benzoate | 100 mg |
| Sodium citrate | q.s. pH to 4.0 |
| Purified water | q.s. 100 ml |

Preparation Procedure

Purified water was warmed, in which citric acid was dissolved to form an acidic solution. Loperamide hydrochloride was dissolved in the acidic solution. The remaining ingredients were then dissolved. The pH was finally adjusted to 4.0 with sodium citrate, whereby a clear syrup was obtained.

EXAMPLE 2

Another syrup was obtained in a similar manner to Example 1 except for the replacement of sucrose by sorbitol.

EXAMPLE 3

A further syrup was obtained in a similar manner to Example 1 except for the replacement of sucrose by glucose.

EXAMPLE 4

A still further syrup was obtained in a similar manner to Example 1 except for the replacement of sucrose by fructose.

COMPARATIVE EXAMPLE 1

A still further syrup was obtained in a similar manner to Example 1 except that the amount of sucrose was reduced to 4.5 g (1,500 times).

TEST 3

Following the procedure of Test 1, the syrups obtained in Examples 1–4 and Comparative Example 1 were orally administered to give the dosage of 0.3 mg/kg in terms of loperamide hydrochloride and their antidiarrheal action were investigated. The results are shown in Table 3.

TABLE 3

Inhibitory Action of Syrups for Diarrhea Induced by Castor Oil in Rats

| Test Syrup | Dosage | Saccharide/loperamide | N* | 1st | 2nd | 3rd | 4th | 5th (hr) |
|---|---|---|---|---|---|---|---|---|
| Control | | | 10 | 0 | 0 | 0 | 0 | 0 |
| Ex. 1 | 0.3 mg/kg | 15,000 time | 10 | 10 | 6 | 2 | 0 | 0 |
| Ex. 2 | 0.3 mg/kg | 15,000 | 10 | 8 | 6 | 2 | 1 | 0 |
| Ex. 3 | 0.3 mg/kg | 15,000 | 10 | 9 | 4 | 2 | 0 | 0 |
| Ex. 4 | 0.3 mg/kg | 15,000 | 10 | 10 | 10 | 9 | 6 | 2 |
| Comp. Ex. 1 | 0.3 mg/kg | 1,500 | 10 | 0 | 0 | 0 | 0 | 0 |

*N: Number of rats

As is apparent from the above results, the syrups of Examples 1–4, which contained the respective saccharides as much as 15,000 times loperamide hydrochloride, had superior antidiarrheal efficacy to the syrup prepared in Comparative Example 1 and containing the saccharide as little as 1,500 times loperamide hydrochloride.

EXAMPLE 5

A suspended syrup of the following formulation was prepared by the below-described preparation procedure.

| <Formulation> | |
|---|---|
| Loperamide hydrochloride | 15 mg |
| Sucrose | 45 g |
| Sodium citrate | 100 mg |
| Polyoxyethylene (160) polyoxy- | 50 mg |
| propylene (30) glycol (Pullonic F68) | |
| Sodium carboxymethylcellulose | 200 mg |
| Crystalline cellulose - sodium carboxymethylcellulose mixture (Avicel RC) | 1 g |
| Butyl paraoxybenzoate | 14 mg |
| Sodium hydroxide | q.s. pH to 7.0 |
| Purified water | q.s. 100 ml |

Preparation Procedure

Purified water was warmed, in which butyl paraoxybenzoate and sucrose were dissolved successively. Avicel RC and sodium carboxymethylcellulose were then added, followed by stirring and dispersion in a homomixer. Next, sodium citrate and Pullonic were dissolved in purified water, followed by the addition and dispersion of loperamide hydrochloride. Both the dispersions were combined and mixed together. The pH of the resultant suspension was adjusted to pH 7.0 with sodium hydroxide, whereby a suspended syrup was obtained.

COMPARATIVE EXAMPLE 2

Another suspended syrup was obtained in a similar manner to Example 5 except that the amount of loperamide hydrochloride was increased to 100 mg.

TEST 4

Following the procedure of Test 1, the suspended syrups obtained in Example 5 and Comparative Example 2 were orally administered to give the dosage of 0.3 mg/kg in terms of loperamide hydrochloride and their antidiarrheal action were investigated. The results are shown in Table 4.

TABLE 4

Inhibitory Action of Suspended Syrups for Diarrhea Induced by Castor Oil in Rats

| Test Suspended Syrup | Dosage | Sucrose/loperamide | N* | 1st | 2nd | 3rd | 4th | 5th (hr) |
|---|---|---|---|---|---|---|---|---|
| Control | | | 10 | 0 | 0 | 0 | 0 | 0 |
| Ex. 5 | 0.3 mg/kg | 3,000 times | 10 | 2 | 2 | 0 | 0 | 0 |
| Comp. Ex. 2 | 0.3 mg/kg | 450 | 10 | 0 | 0 | 0 | 0 | 0 |

*N: Number of rats

As is apparent from the above results, the suspended syrup prepared in Example 5 and containing the saccharide as much as 3,000 times loperamide hydrochloride had superior antidiarrheal efficacy to the suspended syrup prepared in Comparative Example 2 and containing the saccharide as little as 450 times loperamide hydrochloride.

antidiarrheal action were investigated. The results are shown in Table 5.

TABLE 5

| Inhibitory Action of Dry Syrups for Diarrhea Induced by Castor Oil in Rats | | | | | | | | |
|---|---|---|---|---|---|---|---|---|
| Test dry Syrup | Dosage | Sucrose/loperamide | N* | \multicolumn{5}{c}{Number of rats whose diarrhea was inhibited at respective hours after administration of castor oil} |
| | | | | 1st | 2nd | 3rd | 4th | 5th (hr) |
| Control | | | 10 | 0 | 0 | 0 | 0 | 0 |
| Ex. 6 | 0.3 mg/kg | 20,000 times | 10 | 9 | 8 | 6 | 3 | 1 |
| Comp. Ex. 3 | 0.3 mg/kg | 1,000 | 10 | 0 | 0 | 0 | 0 | 0 |

*N: Number of rats

EXAMPLE 6

A dry syrup of the following formulation was prepared by the below-described preparation procedure.

| <Formulation> | |
|---|---|
| Loperamide hydrochloride | 0.05 mg |
| Sucrose | 979.95 mg |
| Sodium hydrogencarbonate | 10 mg |
| Hydroxypropylcellulose | 10 mg |
| Perfume | trace |
| (TOTAL) | 1,000 mg |

Preparation Procedure

Loperamide hydrochloride, sucrose and sodium hydrogencarbonate were combined into an intimate mixture. A solution of hydroxypropylcellulose in purified water was added to the mixture, followed by the addition of the perfume. A dry syrup was then obtained by a wet granulation method.

COMPARATIVE EXAMPLE 3

Another dry syrup was obtained in a similar manner to Example 6 except that the amount of loperamide hydrochloride was increased to 1 mg.

TEST 5

Following the procedure of Test 1, the dry syrups obtained in Example 6 and Comparative Example 3 were orally administered to give the dosage of 0.3 mg/kg in terms of loperamide hydrochloride and their As is apparent from the above results, the dry syrup prepared in Example 6 and containing the saccharide 20,000 times as much as loperamide hydrochloride had superior antidiarrheal efficacy to the dry syrup prepared in Comparative Example 3 and containing the saccharide as little as 1,000 times loperamide hydrochloride.

We claim:

1. An antidiarrheal composition, comprising an amount of a mixture of loperamide hydrochloride and a saccharide selected from the group consisting of fructose, glucose, sucrose, sorbitol, xylitol, mannitol and mixtures thereof effective for the control of diarrhea, said loperamide hydrochloride being present in an amount of from 0.0003 to 0.001 wt. % of said composition and said saccharide being present in an amount of from 9 to about 98 wt. % of said composition and from 20,000 times to 50,000 times the weight of said loperamide hydrochloride.

2. The antidiarrheal composition of claim 1, wherein said saccharide is present in an amount of from 30 to 97.995 wt. % of said composition.

3. The antidiarrheal composition of claim 2, wherein said saccharide is present in an amount of from 30 to 45 wt. % of said composition.

4. The antidiarrheal composition of claim 3, wherein said loperamide hydrochloride is present in an amount of from 0.003 to 0.005 wt. % of said composition.

5. The antidiarrheal composition of claim 1, wherein said loperamide hydrochloride is present in a dosage of from 0.03 to 1.0 mg/kg.

6. The antidiarrheal composition of claim 1, whose preparation form is a syrup or a suspended syrup.

* * * * *